United States Patent [19]

Menon et al.

[11] Patent Number: 4,505,917

[45] Date of Patent: Mar. 19, 1985

[54] FEED COMPOSITIONS CONTAINING A (1-OXO-2-PYRIDYL) DISULFIDE

[75] Inventors: Govind K. Menon, Downingtown, Pa.; Winfred J. Sanders, Mt. Holly, N.J.

[73] Assignee: SmithKline Beckman Corporation, Philadelphia, Pa.

[21] Appl. No.: 420,678

[22] Filed: Sep. 21, 1982

[51] Int. Cl.$^3$ ............... C07D 213/62; C07D 211/72; C07D 211/84; A01N 43/40
[52] U.S. Cl. .................... 514/347; 546/294; 546/261; 546/283; 546/284; 536/4.1; 514/24; 514/335
[58] Field of Search ............ 546/294, 261, 283, 284; 424/263; 426/2, 623, 630, 635

[56] References Cited

U.S. PATENT DOCUMENTS

| | | | |
|---|---|---|---|
| 3,773,770 | 11/1973 | Damico | 424/263 |
| 4,049,665 | 9/1977 | Douglass | 424/263 |
| 4,258,193 | 3/1981 | Fujii et al. | 424/263 |

OTHER PUBLICATIONS

W. Walter et al., Ann. Chem. 727 35–49 (1969).
G. Wagner et al., Z. Chem. 2 86–87, 1967 (Chem. Abs. 58, 5776d).

*Primary Examiner*—Henry R. Jiles
*Assistant Examiner*—Robert C. Whittenbaugh
*Attorney, Agent, or Firm*—William H. Edgerton; Richard D. Foggio; Alan D. Lourie

[57] ABSTRACT

Selected (1-oxo-2-pyridyl) disulfides are used as active ingredients in animal feed compositions and in methods for increasing the growth and feed efficiency of monogastric animals. A useful new compound of this invention is 2-carboxyphenyl (1-oxo-2-pyridyl) disulfide.

16 Claims, No Drawings

FEED COMPOSITIONS CONTAINING A (1-OXO-2-PYRIDYL) DISULFIDE

This invention comprises new animal feed compositions and methods using a (1-oxo-2-pyridyl) disulfide as an active ingredient for altering the metabolic pattern in the digestive tract of monogastric animals, thereby, improving growth and feed efficiency of the animals.

BACKGROUND OF THE INVENTION

Pyridyl disulfides have been described to be good topical antibacterial or antifungal agents for use in shampoos, wound dressings or soaps. Unsymmetrical disulfides for this use are disclosed in M. L. Douglas, U.S. Pat. No. 4,049,665. Column 7, line 66 of the Douglas patent describes the concentration of disulfide in topical compositions to be from 0.1–99%.

Other publications describe topical antimicrobial compositions using certain active ingredients which are also used in the present invention: R. A. Damico, U.S. Pat. No. 3,773,770; W. Walter et al., Ann. Chem. 727 35–49 (1969); G. Wagner et al., Z. Chem. 2 86–7 1967 (Chem. Abs. 58, 5776d). T. Fujii et al., U.S. Pat. No. 4,258,193 discloses certain 2-oxo-pyridyl-amino acid disulfides as intermediates for preparing other disulfides.

The cited publications do not disclose any utility for the active ingredients of this invention which involves internal use as components of supplemented feed compositions to increase the growth of monogastric animals.

DESCRIPTION OF THE INVENTION

The animal feed compositions of this invention are fed to monogastric, growing or fattening, meat-producing animals, especially swine and poultry.

For example, it is known to the art that, during assimilation of food, the production of volatile fatty acids and lactic acid in swine should be relatively low in the upper part of the digestive tract. On the other hand, glucose levels should be higher in the upper tract. Lysine is an essential amino acid which is necessary for growth. Therefore, high levels of lysine are also desirable. Often, corn diets, which are naturally low in lysine, are supplemented with lysine.

The object of this invention is, therefore, to induce relatively low volatile fatty acid production in the upper digestive tract together with a high glucose level, high lysine level and low lactic acid level by administering orally a nontoxic but effective quantity of a selected disulfide to the subject animals. This combination of factors is desired to insure that a larger than normal quantity of energy and amino acid is available to the animals for growth from each unit of food in their diet.

The active ingredients, which are useful in the feed compositions and methods of this invention, are illustrated by the structural formula:

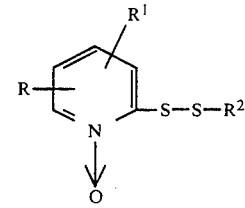

in which:
R and $R^1$ are, each, hydrogen, $C_{1-6}$-alkyl, $C_{1-6}$-alkoxy, $C_{1-6}$-alkylthio, nitro, hydroxy, halo such as chloro or bromo, carboxy, phenyl, benzyl or benzylthio; and
$R^2$ is phenyl, benzyl, pyridyl or 1-oxopyridyl, each of which has one or two substituents as defined for R and $R^1$ above, $C_{1-12}$-alkyl, furyl, thienyl, glucosyl, $C_{3-12}$-alkenyl or carboxy-$C_{1-6}$-alkyl.

A subgeneric group of preferred compounds to be used as active ingredients in this invention are those of formula I in which $R^2$ is not a pyridyl or 1-oxopyridyl. These may be described as unsymmetrical (1-oxo-2-pyridyl) disulfides.

Another aspect of this invention is a subgroup of new chemical compounds which are represented by the following structural formula:

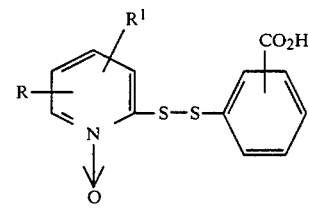

in which R and $R^1$ are, each, as described for formula I.

The active ingredients of formulas I and II are prepared conveniently by the following reaction:

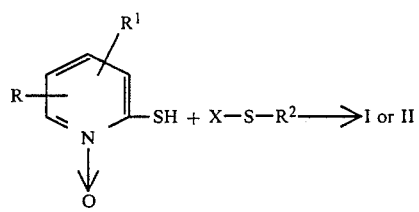

in which R, $R^1$ or $R^2$ are as defined above; and X is chloro or bromo.

The sulfenyl halide, $X-S-R^2$, is conveniently prepared and reacted, in situ, with the mercaptan starting material in an inert organic solvent at a temperature selected from the range of from 0° to the boiling point of the reaction mixture until completion. Base is added to the reaction material to neutralize the reaction product in order to isolate the free base form of the disulfide product. The base or the acid addition salt form of the disulfide, the latter preferably generated from the sulfenyl halide condensation which is outlined above, may be obtained by conventional isolation methods.

Alternatively, certain disulfide active ingredients used in this invention can be prepared by a sulfur/sulfur interchange reaction as described in U.S. Pat. No. 4,258,193 or in the examples hereafter.

Another reference to the preparation of various (1-oxo-2-pyridyl) disulfides is the Damico patent mentioned above.

Also, included in this invention as active ingredients are the nontoxic, stable salts of the compounds of formulas I and II with acids known to the art to be useful for such purposes, for example, the hydrochloride, sulfate, sulfamate, phosphate, nitrate or acetate salts. The salt form, as noted above, may either be formed during the chemical reaction used in the preparation of the chemical ingredients or as a separate step, such as by reacting a compound of formula I with an excess of acid in an organic solvent. Examples of such salts and their preparation are described in U.S. Pat. No. 4,049,665. Also, if a carboxy group is present in the disulfide as in formula II compounds, a nontoxic alkali metal salt may be formed such as by shaking the disulfide with dilute potassium hydroxide, filtering and lyophilizing the filtrate. One skilled in the art will, therefore, recognize that certain compounds which are the active ingredients of this invention will have the capability to form salts and how such salts are prepared and isolated.

In addition of the salt forms of the compounds of this invention, other latentiated or prodrug forms of the active ingredients of formulas I and II may be used such as $C_{1-6}$-alkyl or phenyl esters of acid derivatives. An example of such a latentiated derivative, which has been found to be very active as an active ingredient of this invention, is the 4-nitrophenyl ester of 2-carboxyethyl (1-oxo-2-pyridyl) disulfide.

Examples of chemical compounds which are active ingredients in the feed compositions or methods of this invention are the following: phenyl (1-oxo-2-pyridyl) disulfide, benzyl (1-oxo-2-pyridyl) disulfide, allyl (1-oxo-2-pyridyl) disulfide, 1-butyryl (1-oxo-2-pyridyl) disulfide, methyl (1-oxo-2-pyridyl) disulfide, 3-thienyl (1-oxo-2-pyridyl) disulfide, 4-methoxyphenyl (1-oxo-2-pyridyl) disulfide, 3,4-dichlorobenzyl (1-oxo-2-pyridyl) disulfide, furfuryl (1-oxo-2-pyridyl) disulfide, isopropyl (1-oxo-2-pyridyl) disulfide, 3-pyridyl (1-oxo-2-pyridyl) disulfide, 2,4-dichlorophenyl (1-oxo-2-pyridyl) disulfide, 4-methoxyphenyl (1-oxo-2-pyridyl) disulfide, β-alanyl (1-oxo-2-pyridyl) disulfide, (1-oxo-3-methyl-2-pyridyl) 2,4,6-trimethylphenyl disulfide, (1-oxo-2-pyridyl) carboxymethyl disulfide, (1-oxo-4-methyl-2-pyridyl) (1-oxo-6-methyl-2-pyridyl) disulfide, 2-nitrophenyl (1-oxo-2-pyridyl) disulfide, bis-(3,5-dichloro-1-oxo-2-pyridyl) disulfide, bis-(4-methyl-1-oxo-2-pyridyl) disulfide, bis-(4-carboxy-1-oxo-2-pyridyl) disulfide, (4-benzyl-1-oxo-2-pyridyl) 4-carboxyphenyl disulfide; (4,5-dimethoxy-1-oxo-2-pyridyl) 2-carboxyphenyl disulfide, bis-(4-phenyl-1-oxo-2-pyridyl) disulfide, bis-(5-benzyl-1-oxo-2-pyridyl) disulfide, bis-(3,4,5-trimethyl-1-oxo-2-pyridyl) disulfide, bis-(4,5-dibutoxy-1-oxo-2-pyridyl) disulfide.

The feed compositions of this invention comprise the normal feed rations of the meat producing animals supplemented by a quantity of an active ingredient of formula I, which is effective for improving the growth rate and feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the compound of formula I or the type of feed ration used as the basal feed.

Representative feed rations for swine and poultry are in the examples presented hereafter. Swine feed from weanling to fattening or finishing rations may be supplemented. Swine eat from about 2 lb. per day (for a 25 lb. pig) to 9 lb. per day (for a 150 lb. pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal or soybean meal. The broiler rations, often, contain high energy supplements such as added fats, proteins and vitamins. Turkey rations are similar, but comprise only a starting ration and a growing ration. Chickens or pheasants eat from 0.03-0.3 lbs. of feed per day, turkeys twice that much. Estimated intake of feed is dependent on the weight and age of the meat producing animal.

The active ingredients of formula I are mixed uniformly with such feed rations to give supplemented rations which are, then, fed as to custom which, is, most often, ad libitum. Conveniently, to do this, a premix of the supplemental growth promotant of this invention, optionally combined with or without other supplements known to this art such as an anthelmintic, a nitrogen source or an antibiotic such as virginiamycin or oxytetracycline, is prepared by the manufacturer for sale to the formulators or feed lot operators. The concentration of disulfide in the premix is usually from B 5–75% by weight or a concentration 100–2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ratio which is commonly fed to the target animal. Such premix compositions are included in the term "feed compositions" as used herein.

The concentration of the disulfide of formula I in the complete ration is a nontoxic but active quantity chosen, for example, from a range of about 1–100 parts of active ingredient by weight per million parts of whole feed (ppm) or about 2–115 grams per ton. Advantageously, a quantity is chosen from the range of 5–50 ppm of a disulfide of formula I.

The percentage ratio by weight of active ingredient to feed suggested for this invention is selected from the range of about 0.0001–0.01% which is much lower than the effective range for topical anti-microbial activity described by M. L. Douglas, U.S. Pat. No. 4,049,665 at column 7 line 66, to be 0.1–99% or, preferably, 0.1–3%.

The method of this invention comprises feeding to growing, monogastric, meat-producing animals, especially swine and poultry, an effective growth promoting but nontoxic quantity of a compound of formula I. Other monogastric animals whose digestive tract features fermentation in a cecum or cecum-like chamber are rabbits and horses.

The supplemented feed rations described above are presented to the animal by methods known to the art. Ad libitum feeding in the pasture, pen or growing shed is most convenient to increase the growth rate of the animal and to increase the feed efficiency of the growing operation. Alternatively, the same supplemented feeds may be given to ruminant animals, particularly when the disulfide of formula I is coated to bypass the upper stomach or rumen. Data presented in the in vitro working examples demonstrate that a selective effect as described above was not present in the rumen.

For example, a species active ingredient of this invention, 2-carboxyphenyl (1-oxo-2-pyridyl) disulfide, facilitated growth in chickens and pigs by as much as 6% with a 5–10% improvement in feed efficiency when used as described herein. A concentration of this species in whole feed ration which has proved very effective is about 15–25 ppm.

The following working examples are intended to illustrate this invention. All percentages are by weight. All temperatures are Centigrade.

EXAMPLE 1

A swine ration for growing hogs of 40–100 pounds body weight is prepared using the following formula:

| | |
|---|---|
| Corn, ground | 78.15% |
| Soybean oil meal, 44% | 17.0% |
| Meat scraps, 50% | 3.0% |
| Oyster shell flavor | 0.4% |
| Bone meal | 0.5% |
| Zinc oxide | 0.01% |
| Vitamin A, B, $B_{12}$ & D supplement | optional |

The ration is supplemented to 100% with 20 ppm of 2-carboxyphenyl (1-oxo-2-pyridyl) disulfide distributed through a premix carrier. The ration is fed, ad libitum, to the penned growing or fattening swine.

EXAMPLE 2

A chicken ration for broilers is prepared using the following formula:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin $B_{12}$ | 0.10% |
| Manganese sulfate | 0.02% |
| Vitamin mix | 0.06% |

The ration is supplemented with 20 ppm of 2-carboxyphenyl (1-oxo-N-pyridyl) disulfide and fed ad libitum to the chickens.

EXAMPLE 3

In Vitro Swine Procedure

A. Methodology:

A Yorksire barrow is surgically prepared either with an ileal cannula, which is placed 15 cm. from the ileo-ceco-colic junction, or a cecal cannula, which is placed midway between the apex and origin of the cecum. The animal is fed 4 times daily to restrict intake to 4.5% of body weight in a 30 kg animal or 2.5% of body weight in a 100 kg animal. The swine grower ration is:

| | % w/w | lbs/ton |
|---|---|---|
| Medium ground shelled corn | 70.60 | 1412 |
| Soybean meal, 44% | 22.00 | 440 |
| Dehydrated alfalfa meal, 17% | 4.50 | 90 |
| Calcium propionate | 0.15 | 3 |
| Vitamin/mineral premix | 2.75 | 55 |

Sampling of the material, via the cannula, begins 150–180 minutes following the first morning feeding and continues any time from 30–120 minutes thereafter, depending on the quantity of material needed. The sample is maintained in crushed ice, no cooler than 5°, and is gassed continuously with carbon dioxide. The collected material is filtered. The filtrate is the inoculum used for incubations of the test and control samples. The gassed inoculum, 2.25 ml, is placed in each of 10 gassed test tubes, each containing 0.75 ml of a nutrient solution and 0.5 mg of each test compound. Four blank control tubes, along with the test compound tubes, are incubated 5 hours at 37° with agitation. Four more killed tubes are included which are not incubated.

The tubes are each treated with 0.60 ml of a 25% solution of metaphosphoric acid, then, stored at $-4°$ until analysis. Samples are thawed and centrifuged for 25 minutes at 20,000 r.p.m. The supernatant liquid is decanted, sampled for gas chromatography and automatic analyzing. The results are fed into a computer for finishing to give figures in which the blank control value is 100%. Virginiamycin is used as a positive control.

B. Results:

| | Compound | | | |
|---|---|---|---|---|
| | VFA | LYS | GLU | LAC* |
| | % of control values | | | |
| 1. 2-Carboxyphenyl (1-oxo-2-pyridyl) disulfide | | | | |
| Ileal | | | | |
| (a) 166.7 ppm | 49 | 107 | 999 | 129 |
| (b) 166.7 ppm | 57 | 160 | 235 | 79 |
| (c) 166.7 ppm | 36 | 176 | 190 | 100 |
| (d) 166.7 ppm | 15 | 385 | 152 | 30 |
| Representative Virginiamycin control runs | | | | |
| Ileal | | | | |
| (a) 166.7 ppm | 39 | 289 | 153 | 23 |
| 16.7 ppm | 85 | 212 | 153 | 21 |
| 1.67 ppm | 147 | 134 | 131 | 39 |
| 2. 4-Fluorophenyl (1-oxo-2-pyridyl) disulfide hydrochloride | | | | |
| Ileal | | | | |
| (a) 166.7 ppm | 19 | 246 | 181 | 106 |
| (b) 166.7 ppm | 57 | 200 | 370 | 56 |
| (c) 166.7 ppm | 56 | 104 | 925 | 142 |
| 3. (2,3,4,6-Tetra-O—acetyl-$\beta$-D-glucosyl) (1-oxo-2-pyridyl) disulfide hydrobromide | | | | |
| Ileal | | | | |
| (a) 166.7 ppm | 64 | 174 | 224 | 78 |
| (b) 166.7 ppm | 35 | 147 | 144 | 105 |
| (c) 166.7 ppm | 29 | 123 | 139 | 104 |
| Rumen (Fistulated cattle by method of U.S. Pat. No. 3,615,649) | | | | |
| (d) 50.0 ppm | 70 | 83 | 0 | 364 |
| 5.0 ppm | 104 | 96 | 28 | 249 |
| 0.5 ppm | 108 | 128 | 0 | 107 |
| 4. $\beta$-D-Glucosyl (1-oxo-2-pyridyl) disulfide dihydrate | | | | |
| Ileal | | | | |
| (a) 166.7 ppm | 23 | 321 | 152 | 52 |
| 16.7 ppm | 42 | 294 | 152 | 47 |
| 1.67 ppm | 106 | 114 | 119 | 78 |
| (b) 166.7 ppm | 29 | 107 | 117 | 102 |
| 5. Dodecyl (1-oxo-2-pyridyl) disulfide | | | | |
| Ileal | | | | |
| (a) 166.7 ppm | 39 | 148 | 159 | 105 |
| 16.7 ppm | 50 | 127 | 138 | 107 |
| 1.67 ppm | 68 | 134 | 118 | 104 |
| (b) 166.7 ppm | 26 | 126 | 0 | 141 |
| 6. (5-Bromo-1-oxo-2-pyridyl) disulfide | | | | |
| Ileal | | | | |
| (a) 166.7 ppm | 69 | 81 | 353 | 150 |
| 16.7 ppm | 80 | 90 | 250 | 110 |
| 1.67 ppm | 82 | 92 | 155 | 101 |
| (b) 166.7 ppm | 44 | 122 | 156 | 135 |

-continued

| | | Compound | | | |
|---|---|---|---|---|---|
| | | VFA | LYS | GLU | LAC* |
| | | % of control values | | | |
| (c) | 166.7 ppm | 49 | 119 | 130 | 125 |
| (d) | 166.7 ppm | 103 | 94 | 134 | 94 |
| 7. (1-Oxo-2-pyridyl) disulfide | | | | | |
| Ileal | | | | | |
| (a) | 166.7 ppm | 5 | 212 | 203 | 70 |
| (b) | 166.7 ppm | 17 | 206 | 180 | |
| | 16.7 ppm | 19 | 185 | 180 | |
| | 1.67 ppm | 93 | 121 | 113 | |
| (c) | 166.7 ppm | 4 | 143 | 133 | |
| (d) | 166.7 ppm | 41 | 145 | 625 | 118 |
| | 16.7 ppm | 39 | 134 | 649 | 118 |
| | 1.67 ppm | 84 | 110 | 415 | 110 |
| Rumen | | | | | |
| (e) | 50.0 ppm | 16 | 197 | 999 | 518 |
| (f) | 50.0 ppm | 25 | 65 | 333 | 17 |
| 8. 2-Mercapto-1-oxopyridine | | | | | |
| Ileal | | | | | |
| (a) | 333.3 ppm | 10 | 129 | 100 | 101 |
| (b) | 166.7 ppm | 19 | 175 | 505 | 94 |
| (c) | 166.7 ppm | 31 | 100 | 138 | 101 |

*VFA refers to the total of volatile fatty acids, namely acetate, propionate, isobutyrate, butyrate, isovalerate and valerate. LYS is lysine, GLU is glucose and LAC is L-lactic acid..

C. Conclusions:

These representative results demonstrate the projected spectrum of biological activity of the disulfides, especially compared with that of the parent 1-oxopyridine mercaptan. Inhibition of volatile fatty acid formation is particularly to be noted. Similar studies in the rumen of fistulted cattle, certain of which are noted above, demonstrate that the selective effect is limited to monogastric animals.

EXAMPLE 4

Chick Growth Study

A. Methodology:

512 one day old broiler chicks, selected for weight, health and sex, are housed in an environmentally controlled room with temperature at 80° F. and humidity at 40%. Chicks are fed ad libitum. Water is offered ad libitum. A rye or corn basal ration is fed during the acclimation period (days 1 and 2), then, mixed with the compound under test or control conditions on days 3–17. Either 8 or 16 chicks are used for each test or control group.

| Basal Rye Diet | | |
|---|---|---|
| Diet Ingredients | (% w/w) | (lbs/ton) |
| Ground Rye (fine grind) | 54.6 | 1092 |
| Soybean Meal (49% protein) | 27 | 540 |
| Meat & Bone meal (50% protein) | 10 | 200 |
| Dehydrated Alfalfa meal | 1.25 | 25 |
| Fat, animal | 4 | 80 |
| Dried Whey (or lactose) | 1 | 20 |
| Ground Limestone | 0.67 | 13.4 |
| Dicalcium Phosphate | 0.50 | 10 |
| Iodized salt | 0.23 | 4.6 |
| Vitamin premix | 0.175 | * |
| Trace mineral premix | 0.25 | 5 |
| DL methionine (98%) | 0.25 | 5 |
| Choline Chloride (50% aqueous sol.) | 0.150** | 3 |

*Vitamin premix will be mixed into diets when test chemicals are added. 87.5 g vitamin premix/49,912.5 g of basal rye diet.
**Since choline is added as a 50% aqueous solution, percentage in diet is doubled.

B. Results:

| | | % of Control | |
|---|---|---|---|
| Chemical | | Weight (17 day) | Feed/Grain (3–17 day) |
| 1. Virginiamycin | | | |
| a. | 10 ppm (rye) | 107.1 | 96.5 |
| b. | 50 ppm (rye) | 127.8 | 88.5 |
| c. | 10 ppm (rye) | 97.7 | 100.4 |
| 2. 1-Oxo-2-pyridyl disulfide | | | |
| a. | 2.5 ppm (corn) | 102.2 | 111.4 |
| b. | 1 ppm (rye) | 100.2 | 98.2 |
| | 10 ppm (rye) | 94.7 | 101.9 |
| c. | 1 ppm (rye) | 97.5· | 95.4 |
| | 10 ppm (rye) | 96.6 | 103.1 |
| d. | 20 ppm (rye) | 96.2 | 96.6 |
| e. | 1 ppm (rye) | 100.2 | 98.2 |
| | 10 ppm | 94.7 | 101.9 |
| f. | 2.5 ppm (corn) | 102.2 | 114.4 |
| g. | 2.5 ppm (corn) | 103.0 | 99.8 (31 days) |
| 3. 4-Fluorophenyl (1-oxo-2-pyridyl) disulfide hydrochloride | | | |
| a. | 5 ppm (rye) | 99.4 | 87.5 |
| b. | 10 ppm (rye) | 98.0 | 97.8 |
| c. | 5 ppm (rye) | 99.4 | 87.5 |
| 4. 2-Carboxyphenyl (1-oxo-2-pyridyl) disulfide | | | |
| a. | 10 ppm (rye) | 103.6 | 100.1 |
| b. | 2 ppm (rye) | 100.7 | 102.2 |
| | 5 ppm | 101.6 | 100.6 |
| | 10 ppm | 102.8 | 101.3 |
| | 50 ppm | 98.6 | 102.6 |
| c. | 5 ppm (rye) | 97.2 | 100.0 |
| | 10 ppm | 99.8 | 96.6 |
| | 50 ppm | 86.9 | 107.5 |
| d. | 10 ppm (rye) | 104.2 | 94.2 |
| | 50 ppm | 105.3 | 88.8 |
| | 100 ppm | 54.1 | 179.1 toxic |
| e. | 10 ppm (rye) | 99.5 | 98.8 |
| f. | 6 ppm (rye) | 106.0 | 94.7 |
| 5. 2,3,4,6-Tetra-O—acetyl-β-D-glucosyl (1-oxo-2-pyridyl) disulfide hydrobromide | | | |
| a. | 10 ppm (rye) | 95.4 | 101.6 |

Conclusions:

The tests in chickens confirm the enhancement of either growth rate or increase in feed efficiency of the poultry feed compositions. The 17 day growth rate should be positive and the 3–17 day feed efficiency should be negative. Certain test results are negative due to biological variability in our early or initial screens.

EXAMPLE 5

A. Methodology:

A standard corn based, pre-starter feed composition for feeding 2 week old post weanling pigs was supplemented with 20 ppm of the bis(oxo-2-pyridyl) disulfide. The animal group comprised 15 replications, each containing 3 treatments, which were untreated corn ration as negative control, virginiamycin at 20 ppm as positive control and the stated test ration. Each replication contained 8 treatment groups, in turn, comprising 2 pigs per pen.

The following data summarizes the results:

B. Results:

| | Control | Virginiamycin | (1-oxo-2-pyridyl) disulfide |
|---|---|---|---|
| Dose (ppm | — | 20 | 10 |
| Starting wt (Kg) | 22.3 | 23.4 | 22.2 |
| Average daily gain (0–21 day) | .720 ± .066 | .730 ± .066 | |
| Average daily gain | .725 | .746 | .716 |
| Feed/gain | 2.95 | 2.80 | 2.84 |
| (0–41 day) | | | |
| Average daily gain | .749 | .747 | .723 |
| Feed/gain | 3.36 | 3.32 | 3.26 |

-continued

|  | Control | Virginiamycin | (1-oxo-2-pyridyl) disulfide |
|---|---|---|---|
| (0–63 day) |  |  |  |

EXAMPLE 6

A. Methodology:

15 Replications of swine each containing 3 treatments test compositions containing 20 ppm of 2-carboxyphenyl (1-oxo-2-pyridyl) disulfide (CPD).

B. Results:

|  | Control | Virginiamycin | CPD |
|---|---|---|---|
| Dose | — | 10 ppm | 20 ppm |
| Starting wt | 23.7 | 22.51 | 23.17 |
| Average daily gain | .704 | .697 | .690 |
| Feed/gain (0–21 day) | 2.70 | 2.61 | 2.65 |
| Average daily gain | .691 | .719 | .720 |
| Feed/gain (0–35 day) | 2.85 | 2.82 | 2.83 |

C. Conclusions:

2-Carboxyphenyl (1-oxo-2-pyridyl) disulfide (CPD) demonstrated increased growth and feed efficiency roughly equivalent with that of virginiamycin.

EXAMPLE 7

Chemical Preparations

A. A round bottom flask equipped with mechanical stirrer was charged with 3.08 g (0.020 mol) of 2-mercaptobenzoic acid and 100 ml of anhydrous ether. The mixture was stirred until the thiosalicylate dissolved. To this solution was added 4.45 g (0.025 mol) of N-bromosuccinimide. After 60 minutes, the orange solution which contains 2-carboxybenzenesulfenyl bromide was decanted from the succinimide precipitate. To the orange etherate solution was added 2.5 g (0.020 mol) of 2-mercaptopyridine-N-oxide. After 90 minutes of vigorous agitation at 25°, a 85% yield of 2-carboxyphenyl (1-oxo-2-pyridyl) disulfide was collected by filtration. The disulfide had a melting point of 145°–147°. Compound is further purified by recrystallization from 8:1:1:1 (8 parts methanol to 1 part methylene chloride, ether and acetic acid respectively) solution. The purified compound had a melting point of 145°–146°.

Anal. Calcd. for $C_{12}H_9NO_3S_2$: C, 51.60; H, 3.25; N, 5.01; S, 22.95. Found: C, 51.47; H, 3.28; N, 5.12; S, 22.82.

The above procedure is repeated using 3-mercaptobenzoic acid and 4-mercaptobenzoic acid to give, respectively, 3-carboxyphenyl (1-oxo-2-pyridyl) disulfide and 4-carboxyphenyl (1-oxo-2-pyridyl) disulfide.

B. In a round bottom flask was placed 500 mg (0.0027 mol) of N-bromosuccinimide, 1 g (0.0028 mol) of β-thioglucose tetraacetate and 50 ml of toluene. The mixture was mechanically stirred for 20 minutes while the temperature was lowered to 0°. To this cooled solution is added, from a dropping funnel, 340 mg (0.0027 mol) of 2-mercaptopyridine-N-oxide in 50 ml of toluene. After 20 minutes at 5° or below, the temperature was raised to 60° and stirring was continued for an additional 20 minutes. The reaction mixture was cooled to room temperature and stirred overnight. A white precipitate was collected and thin layer chromatography showed one spot (using a silica gel plate with eluting solvent of 8:1:1:1 methylene chloride:methanol; ethyl ether; acetic acid). Crude melting point was 160°–163°. The product was further purified by recrystallization from methanol and anhydrous ether (1:2 ratio). The final product was vacuum oven dried for 24 hours to give preparation of (2,3,4,6-tetra-O-acetyl-β-D-glucosyl) (1-oxo-2-pyridyl) disulfide hydrobromide, m.p. 154°–155°.

Anal. Calcd. for $C_{19}H_{23}NO_{10}S_2 \cdot HBr$: C, 40.00; H, 4.24; N, 2.45. Found: C, 39.70; 40.12; H, 4.17, 4.17; N, 2.26, 2.39.

C. (2,3,4,6-Tetra-O-acetyl-β-D-glucosyl) (1-oxo-2-pyridyl) disulfide (250 mg) was deacetylated by dissolving the compound in methanol and bubbling in hydrogen chloride gas. After 10 minutes, the gas was removed and mixture stirred overnight. Methanol was removed by rotary evaporation and clear solid is dried under nitrogen vacuum. The compound has a melting point of 87°; (β-D-glucosyl) (1-oxo-pyridyl) disulfide dihydrate.

Anal. Calcd. for $C_{11}H_{15}NO_6S_2 \cdot 2.5\ H_2O$: C, 36.06; H, 4.95; N, 3.82. Found: C, 36.11; H, 4.65; N, 3.78.

D. N-chlorosuccinimide (4.39 g) was added in several portions to a cold (0°) solution of 4.26 g (0.032 mol) of 97% p-fluorothiophenol and 100 ml of toluene. After 40 minutes stirring at room temperature, the orange solution was collected by filtration, cooled to 0° while a solution of 2.11 g of mercaptopyridine-N-oxide in 100 ml of ether was added. After stirring at room temperature for 20 minutes, the product was collected, washed and purified over a silica gel column to give 5.27 g of 4-fluorophenyl (1-oxo-2-pyridyl) disulfide, m.p. 94°–96°.

Anal. Calcd. for $C_{11}H_8NOSF \cdot HCl$: C, 52.16; H, 3.18; N, 5.53. Found: C, 52.07; H, 3.27; 5.63.

E. Using the same procedure as above, dodecyl (1-oxo-2-pyridyl) disulfide hydrobromide was obtained; m.p. 103°–105°.

Anal. Calcd. for $C_{17}H_{29}NOS_2 \cdot HBr$: C, 42.97; H, 7.40; N, 3.43. Found: C, 50.40, 50.28; H, 7.07, 7.30; N, 3.40, 3.38.

F. A mixture of 8.6 g (0.034 mol of bis(1-oxo-2-pyridyl) disulfide, 6.9 (0.056 mol) of 3-mercaptopropionate and 400 ml of chloroform was heated at reflux overnight. Cooling separated a product contaminated with disulfide starting material. The mixture was purified by recrystallization from hot methanol to give 2-carboxyethyl (1-oxo-2-pyridyl) disulfide, m.p. 162°–163°.

Anal. Calcd. for $C_8H_9NO_3S_2$: C, 41.56; N, 3.89; N, 6.06; S, 27.70. Found: C, 51.54; H, 3.94; N, 6.05; S, 27.85.

The 4-nitrophenyl ester derivative melts at 109°–111°.

Anal. Calcd. for $C_{14}H_{12}N_2O_5S_2$: C, 47.27; H, 3.43; N, 7.95. Found: C, 47.89; H, 3.60; N, 7.94.

What is claimed is:

1. The method of improving the weight gain and feed efficiency of meat-producing monogastric animals comprising feeding to said animals an effective but nontoxic quantity of a compound of the formula:

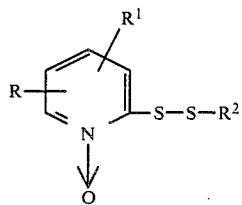

in which:

R and $R^1$ are, each, hydrogen, $C_{1-6}$-alkyl, $C_{1-6}$-alkoxy, $C_{1-6}$-alkylthio, nitro, hydroxy, halo, carboxy, phenyl, benzyl or benzylthio; and $R^2$ is a phenyl, benzyl, pyridyl, 1-oxo-pyridyl, each of the former has one or two optional substituents as defined for R and $R^1$ above, $C_{1-12}$-alkyl, furyl, thienyl, glucosyl, alanyl, $C_{3-12}$-alkenyl or carboxy-$C_{1-6}$-alkyl; or a nontoxic, stable salt thereof.

2. The method of claim 1 in which the compound is fed in the form of an animal feed ration containing from 5-50 parts of compound per million parts of ration by weight.

3. The method of claim 1 in which the compound is carboxyphenyl (1-oxo-2-pyridyl) disulfide or a nontoxic salt thereof.

4. The method of claim 1 in which the compound is the 2-carboxyphenyl (1-oxo-2-pyridyl) disulfide which is fed in the form of an animal feed ration containing from 15-25 parts of compound per million parts of ration by weight.

5. The method of claim 1 in which $R^2$ is a substituted phenyl.

6. An animal feed composition supplemented by a quantity of a compound as defined in claim 1 which is effective for increasing the growth rate and feed efficiency of a meat producing monogastric animal but which is nontoxic to said animal.

7. The composition of claim 6 in which quantity of the compound is selected from the range of from 1-100 parts of compound per million parts of composition by weight.

8. The composition of claim 6 in which the compound is a carboxyphenyl (1-oxo-2-pyridyl) disulfide.

9. The composition of claim 6 in which the compound is 2-carboxyphenyl (1-oxo-2-pyridyl) disulfide which is present in from 15-25 parts of compound per million parts of composition.

10. The composition of claim 6 in which the composition is a whole feed ration.

11. The composition of claim 6 in which the composition is a premix composition.

12. A compound of the formula:

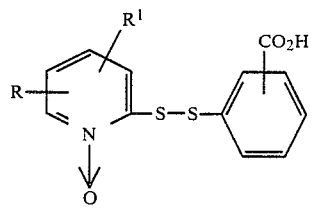

in which:

R and $R^1$ are, each, hydrogen, $C_{1-6}$-alkyl, $C_{1-6}$-alkoxy, $C_{1-6}$-alkylthio, nitro, hydroxy, halo, carboxy, phenyl, benzyl or benzylthio; or a nontoxic salt thereof.

13. The compound of claim 12 in which R and $R^1$, are hydrogen.

14. The compound of claim 12 in which R and $R^1$ are, each, hydrogen, methyl or methoxy.

15. The compound of claim 12 being 2-carboxyphenyl (1-oxo-2-pyridyl) disulfide.

16. 2-Carboxyethyl (1-oxo-2-pyridyl) disulfide, its phenyl or lower alkyl esters.

* * * * *